United States Patent
Joshi et al.

(10) Patent No.: US 6,562,983 B1
(45) Date of Patent: May 13, 2003

(54) PROCESS FOR THE PREPARATION OF ALKYL 4[2-(PHTHALIMIDO)ETHOXY]-ACETOACETATE

(75) Inventors: Rohini Ramesh Joshi, Maharabittra (IN); Ramesh Anna Joshi, Maharashtra (IN); Ravindranathan Thottappillil, Maharashtra (IN)

(73) Assignee: Council of Scientific and Industrial Research, New Delphi (IN)

( * ) Notice: Subject to any disclaimer, the term of this patent is extended or adjusted under 35 U.S.C. 154(b) by 0 days.

(21) Appl. No.: 10/098,498

(22) Filed: Mar. 18, 2002

(51) Int. Cl.$^7$ ............................................. C07D 209/12
(52) U.S. Cl. ....................................................... 548/485
(58) Field of Search .......................................... 548/485

(56) References Cited

U.S. PATENT DOCUMENTS 4,572,909 A * 2/1986 Campbell et al. ........... 544/333

* cited by examiner

*Primary Examiner*—Patricia L. Morris
(74) *Attorney, Agent, or Firm*—Burns, Doane, Swecker & Mathis, L.L.P.

(57) ABSTRACT

The present invention provides a method to prepare alkyl-4-[2(phthalimido)-ethoxy]-acetoacetate which are useful in the manufacture of anti-hypertensive and anti-ischaemic drugs by reacting 2(phthalimido)-ethoxyacetic acid with thionyl chloride and then reacting the acid chloride product obtained with Meldrums acid.

6 Claims, No Drawings

PROCESS FOR THE PREPARATION OF ALKYL 4[2-(PHTHALIMIDO)ETHOXY]-ACETOACETATE

FEILD OF THE INVENTION

This invention relates to the method for the preparation of alkyl 4[2-(phthalimido)ethoxy]-acetoacetate. More particularly it relates to the preparation of ethyl-4-[2(phthalimido)ethoxy]-acetoacetate having formula (4)

Formula (4)

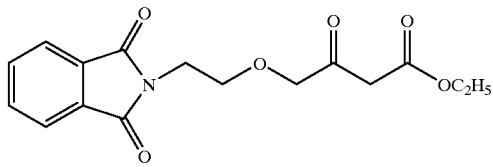

using 4-[2(phthalimido)-ethoxyacetic acid of formula (1).

Formula (1)

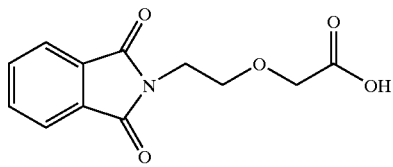

BACKGROUND OF THE INVENTION

Ethyl-4-[2(phthalimido)ethoxy]-acetoacetate (4) is an important intermediate in the manufacture of anti-ischaemic and antihypertensive drug i.e. amlodipine having formula (5).

Formula (5)

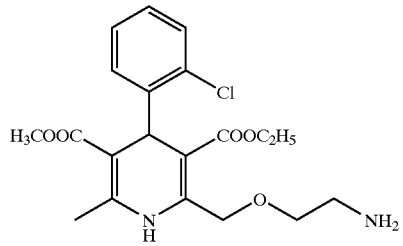

In the prior art processes, ethyl 4-[2(phthalimido)-ethoxy] acetoacetate (4) has been hitherto obtained by O-alkylation of N-(2-hydroxyethyl) phthalimide with ethyl 4-chloroacetoacetate using sodium hydride as base (Simon F, Campbell, Peter E. Cross, John K. Stubs, U.S. Pat. No. 4,572,909).

The draw backs of the known processes are 1) the use of sodium hydride as base which is known to be pyroforic and 2) the alkylating agent ethyl-4-chloroacetoacetate is known to have high toxicity (Oyo Yakuri, CA 107:110714, 1987).

The toxic symptoms consisted of the inhibition of CNS systems especially respiratory depression and the local irritation of tissues. The O-alkylation is carried out in anhydrous THF and reaction conditions are stringent (−10° C.).

OBJECTS OF THE INVENTION

The main object of the present invention is to prepare of alkyl 4-[2(phthalimido)-ethoxy]-acetoacetate of formula (4) using easily available raw materials.

It is another object of the invention to provide a process for the preparation of alkyl 4-[2(phthalimido)-ethoxy]-acetoacetate of formula (4) using easily available raw materials such as phthalimide, solvent such as toluene and base such as potassium carbonate, Meldrum acid and thionyl chloride, which overcomes the drawbacks of the prior art methods enumerated above.

SUMMARY OF THE INVENTION

Accordingly the present invention provides an improved process for the preparation of alkyl-4-[2(phthalimido)-ethoxy]-acetoacetate having formula (4), Formula (4)

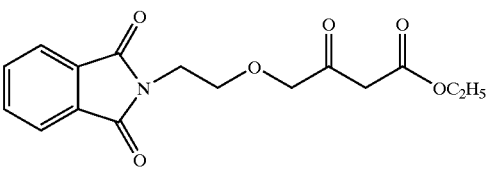

which comprises reacting 2-(phthalimido)-ethoxyacetic acid of the formula (1)

Formula (1)

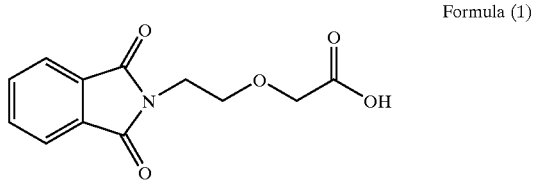

with thionyl chloride to obtain the compound having formula (2)

Formula (2)

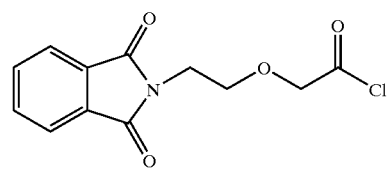

followed by reacting compound of formula (2) with Meldrum's acid having formula (3)

Formula (3)

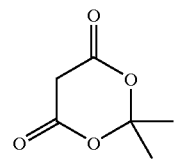

in an organic solvent in the presence of a base at a temperature ranging between 5–10° C., acidifying with dilute HCl, extracting in an organic solvent, removing the solvent and refluxing the residue with alcohol to obtain the desired product.

In one embodiment of the invention the 2[(2-phthalimido) ethoxy]acetic acid of formula (1) is reacted with thionyl chloride in the presence of an organic solvent.

In another embodiment of the invention, the solvent used for the reaction of 2[(2-phthalimido)ethoxy]acetic acid of formula (1) is selected from toluene, dimethyl formamide and a mixture thereof.

In another embodiment of the invention, the organic solvent used for the reaction of compound of formula (2) with Meldrums acid of formula (3) is selected from ethylenedichloride and methylenedichloride.

In another embodiment of the invention, the organic solvent used for the extraction of alkyl-4-[2(phthalimido)-ethoxy]-acetoacetate having formula (4) is selected from ethylenedichloride, methylenedichloride and toluene.

In another embodiment the base used for the reaction of compound of formula (2) with Meldrums acid of formula (3) is selected from triethylamine and pyridine.

DETAILED DESCRIPTION OF THE INVENTION

The invention provides a method to prepare various alkyl-4-[2(phthalimido)-ethoxy]-acetoacetate (4) useful in the manufacture of anti-hypertensive and anti-ischaemic drugs. The present investigation consists of an improved and elegant process for the preparation of alkyl-4-[2 (phthalimido)-ethoxy]acetoacetate (4).

The process of the present invention is described herein below with reference to examples which are illustrative only and should not be construed to limit the scope of the present invention in any manner.

EXAMPLE -1

A: To the suspension of 2[(2-phthalimido)ethoxy]acetic acid (1), (100 parts, 0.4 mole part) in toluene (1000 parts) and dimethyl formamide (1 part), thionyl chloride (108 parts, 1.46 mol. part) was slowly added with stirring at room temperature. After complete addition of thionyl chloride the reaction mixture was heated at 60° C. for three hours. The reaction mixture was concentrated under reduced pressure. The residue (2) after cooling to room temperature was dissolved in methylene dichloride (900 parts).

B. Meldrum's acid (3), (50 parts, prepared according to procedure reported in Attila G. Relenyi, David E. Wallick and Jill D. Streit, U.S. Pat. No. 4613,671) was added to a solution of pyridine (100 parts) in methylene dichloride (400 parts) cooled to 5–10° C. under nitrogen atmosphere. After stirring for 30 minutes the acid chloride solution (2), (1000 parts) was slowly added over a period of one hour maintaining the temperature at 5–10° C. Stirring was continued for additional one hour. The reaction mixture was acidified by addition of 2N HCI (400 parts). The layers were separated. The methylene dichloride extract was washed with 2N HCI (120 parts, 2 times) followed by water concentrated under reduced pressure. The residue (130 parts) followed by water concentrated under reduced pressure. The residue (130 parts) was dissolved in anhydrous ethyl alcohol (200 parts) and the resulting solution was refluxed for one hour. The completion of the reaction was followed by TLC (silica gel, ethyl acetate: petroleum ether 40.60 as eluent Rf: product 0.7, stating material 0.1). The solution was concentrated under reduced pressure and the residue was extracted with toluene (250 parts, 3 times). The combined toluene extract was washed with water (100 parts, 2 times) saturated sodium bicarbonate (100 parts), dried over anhydrous sodium sulphate and concentrated under reduced pressure. The residue (4), (100 parts) was used as such for Hantzsch condensation giving phthaloyl amlodipine which is known precursor for amlodipine besylate.

$^1$H NMR (CDCl$_3$), values: 7.80 (4H, m), 4.15 (2H,S), 4.10 (2H, q) 3.92 (2H, t), 3.78(2H, t), 3.49 (2H, S) 1.22 (3H, t).

EXAMPLE -2

A: To a suspension of 2[(2-phathalimido)ethoxy]acetic acid (1), (100 parts, 0.4 mole part) in toluene (100 parts) and dimethyl formamide (I part), thionyl chloride (108 parts, 1.46 mol. Part) was slowly added with stirring at room temperature. After complete addition of thionyl chloride the reaction mixture was heated at 60° C. for three hours. The reaction mixture was concentrated under reduced pressure. The residue (2) after cooling to room temperature was dissolved in ethylenedichloride (900 parts).

B. Meldrum's acid (3), (50 parts, prepared according to procedure reported in Attila G. Relenyi, David E. Wallick and Jill D. Streit, U.S. Pat. No. 4,613,671) was added to a solution of triethylamine (100 parts) in ethylene dichloride (400 parts) cooled to 5–10° C. under nitrogen atmosphere. After stirring for 30 minutes the acid chloride solution (2), (1000 parts) was slowly added over a period of one hour maintaining the temperature at 5–10° C. Stirring was continued for additional one hour. The reaction mixture was acidified by addition of 2N HCI (400 parts). The layers were separated. The ethylenedichloride extract was washed with 2N HCI (120 parts, 2 times) followed by water concentrated under reduced pressure. The residue (130 parts) was dissolved in anhydrous ethyl alcohol (200 parts) and the resulting solution was refluxed for one hour. The completion of the reaction was followed by TLC (silica gel, ethyl acetate: petroleum ether 40.60 as elunent Rf: product 0.7, starting material 0.1). The solution was concentrated under reduced pressure and the residue was extracted with toluene (250 parts, 3 times). The combined toluene extract was washed with water (100 parts, 2 times), saturated sodium bicarbonate (100 parts), dried over anhydrous sodium sulphate and concentrated under reduced pressure. The residue (4), (100 parts) was used as such for Hantzsch condensation giving phthaloyl amlodipine which is known precursor for amlodipine besylate.

ADVANTAGES

1. Easily accessible and commercially available raw materials,
2. Ease of handling of raw materials
3. Ease in scale up and commercial production.

We claim:

1. A process for the preparation of alkyl-4-[2 (phthalimido)-ethoxy]-acetoacetate of the formula 4, Formula (4)

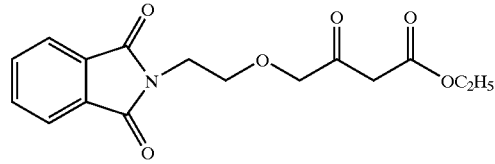

which comprises reacting 2(phthalimido)-ethoxyacetic acid (1)

Formula (1)

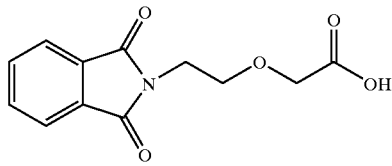

with thionyl chloride to obtain a compound of formula 2,

Formula (2)

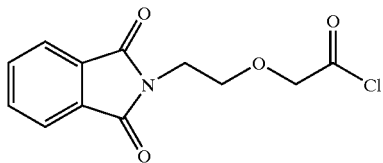

reacting compound of formula (2) with Meldrum acid of formula (3)

Formula (3)

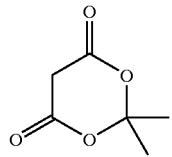

in an organic solvent in the presence of a base at temperature ranging between 5–10° C., acidifying with dilute HCI, followed by extracting in an organic solvent, removing the solvent and refluxing the residue with an alcohol to obtain the desired product of formula (4).

2. A process claimed in claim 1 wherein 2[(2-phthalimido)ethoxy]acetic acid of formula (1) is reacted with thionyl chloride in the presence of an organic solvent.

3. A process claimed in claim 2 wherein the organic solvent used for the reaction of 2[(2-phthalimido)ethoxy] acetic acid of formula (1) is selected from toluene, dimethyl formamide and a mixture thereof.

4. A process claimed in claim 1 wherein the organic solvent used for the reaction of compound of formula (2) with Meldrums acid of formula (3) is selected from ethylenedichloride and methylenedichloride.

5. A process claimed in claim 1 wherein the organic solvent used for the extraction of alkyl-4-[2(phthalimido)-ethoxy]-acetoacetate having formula (4) is selected from ethylenedichloride, methylenedichloride and toluene.

6. A process claimed in claim 1 wherein the base used for the reaction of compound of formula (2) with Meldrums acid of formula (3) is selected from triethylamine and pyridine.

\* \* \* \* \*